US011654246B2

(12) United States Patent
Revellat et al.

(10) Patent No.: US 11,654,246 B2
(45) Date of Patent: May 23, 2023

(54) DRUG DELIVERY DEVICE

(71) Applicant: SANOFI, Paris (FR)

(72) Inventors: Hugo Revellat, Cambridgeshire (GB); Thomas Mark Kemp, Cambridgeshire (GB); William Timmis, Cambridgeshire (GB)

(73) Assignee: Sanofi, Paris (FR)

( * ) Notice: Subject to any disclaimer, the term of this patent is extended or adjusted under 35 U.S.C. 154(b) by 292 days.

(21) Appl. No.: 16/759,488

(22) PCT Filed: Nov. 1, 2018

(86) PCT No.: PCT/EP2018/079915
§ 371 (c)(1),
(2) Date: Apr. 27, 2020

(87) PCT Pub. No.: WO2019/086561
PCT Pub. Date: May 9, 2019

(65) Prior Publication Data
US 2020/0289764 A1 Sep. 17, 2020

(30) Foreign Application Priority Data
Nov. 3, 2017 (EP) .................................. 17306518

(51) Int. Cl.
*A61M 5/315* (2006.01)
*A61M 5/20* (2006.01)
*A61M 5/32* (2006.01)

(52) U.S. Cl.
CPC ........ *A61M 5/3157* (2013.01); *A61M 5/2033* (2013.01); *A61M 5/3243* (2013.01);
(Continued)

(58) Field of Classification Search
CPC .............. A61M 5/3157; A61M 5/2033; A61M 5/3243; A61M 2005/2013;
(Continued)

(56) References Cited

U.S. PATENT DOCUMENTS 4,629,454 A 12/1986 Grier
4,693,711 A 9/1987 Bremer et al.
(Continued)

FOREIGN PATENT DOCUMENTS

CN 200987443 12/2007
CN 101107032 1/2008
(Continued)

OTHER PUBLICATIONS

National Standards of People's Republic of China, "Audible and/or Visual Fire Alarm Signaling Appliances", General Administration of Quality Supervision, Inspection and Quarantine of the People's Republic of China, Jul. 2011, 39 pages (with machine translation).
(Continued)

*Primary Examiner* — Bhisma Mehta
*Assistant Examiner* — Nidah Hussain
(74) *Attorney, Agent, or Firm* — Fish & Richardson P.C.

(57) ABSTRACT

The present specification relates to a drug delivery device including a housing adapted to receive a primary container with a piston, a plunger slidably disposed in the housing and adapted to drive the piston for delivering a medicament, a drive spring pre-loaded between the housing and the plunger so as to urge the plunger in a distal direction, an audible and/or tactile indicator, and a trigger mechanism arranged between the indicator and the plunger. The trigger mechanism is configured to support the indicator in an initial state of the device and during delivery of the medicament and to couple with the plunger to activate the audible and/or tactile indicator at or near an end of delivery.

20 Claims, 7 Drawing Sheets

(52) U.S. Cl.
CPC ............... *A61M 2005/2013* (2013.01); *A61M 2205/581* (2013.01); *A61M 2205/582* (2013.01)

(58) Field of Classification Search
CPC ...... A61M 2205/581; A61M 2205/582; A61M 2205/43
USPC .......................................................... 604/192
See application file for complete search history.

(56) References Cited

U.S. PATENT DOCUMENTS

| | | | |
|---|---|---|---|
| 4,810,249 | A | 3/1989 | Haber et al. |
| 5,114,406 | A | 5/1992 | Gabriel et al. |
| 5,116,313 | A | 5/1992 | McGregor |
| 5,127,906 | A | 7/1992 | Landry et al. |
| 5,271,527 | A | 12/1993 | Haber et al. |
| 5,391,157 | A | 2/1995 | Harris et al. |
| 7,611,495 | B1 | 11/2009 | Gianturco |
| 8,979,807 | B2 | 3/2015 | Grunhut et al. |
| 9,168,339 | B2 | 10/2015 | Cowe |
| 9,199,038 | B2 | 12/2015 | Daniel |
| 9,216,251 | B2 | 12/2015 | Daniel |
| 9,744,306 | B2 | 8/2017 | Cowe |
| 9,764,096 | B2 | 9/2017 | Maritan |
| 10,888,668 | B2 | 1/2021 | Mosebach et al. |
| 10,918,811 | B2 | 2/2021 | Mosebach et al. |
| 10,926,032 | B2 | 2/2021 | Mosebach et al. |
| 11,357,922 | B2 | 6/2022 | Mosebach et al. |
| 11,400,232 | B2 | 8/2022 | Schader et al. |
| 2004/0210199 | A1 | 10/2004 | Atterbury et al. |
| 2005/0027255 | A1* | 2/2005 | Lavi ..................... A61M 5/326 604/135 |
| 2007/0088248 | A1 | 4/2007 | Glenn et al. |
| 2008/0021373 | A1 | 1/2008 | Rosati |
| 2010/0198182 | A1 | 8/2010 | Lanigan et al. |
| 2011/0026721 | A1 | 2/2011 | Parker |
| 2011/0105952 | A1 | 5/2011 | Bernstein et al. |
| 2013/0023749 | A1 | 1/2013 | Afanasewicz et al. |
| 2013/0090605 | A1 | 4/2013 | O'Connor et al. |
| 2013/0906605 | | 4/2013 | O'Connor et al. |
| 2013/0345642 | A1 | 12/2013 | Cowe |
| 2014/0114250 | A1 | 4/2014 | DeSalvo et al. |
| 2014/0243751 | A1 | 8/2014 | Brereton et al. |
| 2014/0276568 | A1 | 9/2014 | Worden et al. |
| 2015/0265772 | A1 | 9/2015 | Maritan |
| 2016/0008541 | A1 | 1/2016 | Hirschel et al. |
| 2016/0008542 | A1 | 1/2016 | Hirschel et al. |
| 2016/0015899 | A1 | 1/2016 | Plumptre et al. |
| 2016/0144133 | A1 | 5/2016 | Kemp |
| 2018/0154078 | A1 | 6/2018 | Mosebach et al. |
| 2021/0093790 | A1 | 4/2021 | Mosebach et al. |
| 2021/0128837 | A1 | 5/2021 | Mosebach et al. |
| 2021/0170115 | A1 | 6/2021 | Mosebach et al. |
| 2022/0257865 | A1 | 8/2022 | Mosebach et al. |
| 2022/0305206 | A1 | 9/2022 | Schader et al. |

FOREIGN PATENT DOCUMENTS

| | | |
|---|---|---|
| CN | 201111673 | 9/2008 |
| CN | 201243374 | 5/2009 |
| CN | 102209564 | 10/2011 |
| CN | 102842236 | 12/2012 |
| CN | 202887394 | 4/2013 |
| CN | 103177716 | 6/2013 |
| CN | 103235538 | 8/2013 |
| CN | 104080499 | 10/2014 |
| CN | 104519929 | 4/2015 |
| CN | 105188809 | 12/2015 |
| CN | 105327432 | 2/2016 |
| CN | 105451792 | 3/2016 |
| CN | 106573114 | 4/2017 |
| DE | 7833454 | 5/1979 |
| DE | 3935672 | 11/1990 |
| EP | 2727617 | 5/2014 |
| EP | 2868338 | 5/2015 |
| EP | 3302632 | 9/2020 |
| JP | H06-190041 | 7/1994 |
| JP | H07-509636 | 10/1995 |
| JP | 2005-508205 | 3/2005 |
| JP | 2011-519712 | 7/2011 |
| JP | 2012-504006 | 2/2012 |
| JP | 2013-526894 | 6/2013 |
| JP | 2013-526904 | 6/2013 |
| JP | 2013-146600 | 8/2013 |
| JP | 2013-534164 | 9/2013 |
| JP | H5-508098 | 5/2014 |
| JP | 2014-526298 | 10/2014 |
| JP | 2014-531961 | 12/2014 |
| JP | 2015-536184 | 12/2015 |
| JP | 2016-512766 | 5/2016 |
| JP | 2016-513507 | 5/2016 |
| JP | 2016-526460 | 9/2016 |
| RU | 2140794 | 11/1999 |
| RU | 2012137269 | 3/2014 |
| WO | WO 92/17223 | 10/1992 |
| WO | WO 94/03222 | 2/1994 |
| WO | WO 02/092153 | 11/2002 |
| WO | WO 2005/046773 | 5/2005 |
| WO | WO 2006/079481 | 8/2006 |
| WO | WO 2009/140251 | 11/2009 |
| WO | WO 2010/035057 | 4/2010 |
| WO | WO 2011/079278 | 6/2011 |
| WO | WO 2011/123024 | 10/2011 |
| WO | WO 2012/022810 | 2/2012 |
| WO | WO 2012/045350 | 4/2012 |
| WO | WO 2013/034984 | 3/2013 |
| WO | WO 2013/057032 | 4/2013 |
| WO | WO 2013/057033 | 4/2013 |
| WO | WO 2013/057034 | 4/2013 |
| WO | WO 2014/005808 | 1/2014 |
| WO | WO 2014/066461 | 5/2014 |
| WO | WO 2014/139914 | 9/2014 |
| WO | WO 2014/139922 | 9/2014 |
| WO | WO 2014/146209 | 9/2014 |
| WO | WO 2014/164943 | 10/2014 |
| WO | WO 2015/004049 | 1/2015 |
| WO | WO 2015/004050 | 1/2015 |
| WO | WO 2015/019071 | 2/2015 |
| WO | WO 2015/062915 | 5/2015 |
| WO | WO 2016/001304 | 1/2016 |
| WO | WO 2016/193343 | 12/2016 |
| WO | WO 2016/193344 | 12/2016 |
| WO | WO 2016/193346 | 12/2016 |

OTHER PUBLICATIONS

National Standards of People's Republic of China, "Fire Detection and Alarm Systems—Smoke Alarms", General Administration of Quality Supervision, Inspection and Quarantine of the People's Republic of China, Jul. 2006, 45 pages (with machine translation).
National Standards of People's Republic of China, "Vehicle Electronic Sirens", General Administration of Quality Supervision, Inspection and Quarantine of the People's Republic of China, Dec. 2014, 31 pages (with machine translation).
PCT International Preliminary Report on Patentability in International Appln. No. PCT/EP2018/079915, dated May 5, 2020, 8 pages.
Karpova, "The basics of surdopedagogy", Ekaterinburg, pp. 20-21, 2008.
PCT International Preliminary Report on Patentability in International Appln. No. PCT/EP2016/062449, dated Dec. 5, 2017, 6 pages.
PCT International Preliminary Report on Patentability in International Appln. No. PCT/EP2016/062450, dated Dec. 5, 2017, 7 pages.
PCT International Preliminary Report on Patentability in International Appln. No. PCT/EP2016/062452, dated Dec. 5, 2017, 7 pages.

(56) References Cited

OTHER PUBLICATIONS

PCT International Preliminary Report on Patentability in International Appln. No. PCT/EP2016/062454, dated Dec. 5, 2017, 7 pages.
PCT International Preliminary Report on Patentability in International Appln. No. PCT/EP2018/079917, dated May 5, 2020, 8 pages.
PCT International Search Report and Written Opinion in International Appln. No. PCT/EP2016/062449, dated Aug. 17, 2016, 8 pages.
PCT International Search Report and Written Opinion in International Appln. No. PCT/EP2016/062450, dated Aug. 5, 2016, 9 pages.
PCT International Search Report and Written Opinion in International Appln. No. PCT/EP2016/062452, dated Sep. 15, 2016, 11 pages.
PCT International Search Report and Written Opinion in International Appln. No. PCT/EP2016/062454, dated Aug. 5, 2016, 9 pages.
PCT International Search Report and Written Opinion in International Appln. No. PCT/EP2018/079917, dated Dec. 5, 2018, 10 pages.
International Search Report and Written Opinion in Application No. PCT/EP2018/079915, dated Dec. 5, 2018, 13 pages.
Engineers Edge, "Transducers USA Announced Improved TRIP60 Series of Audio Alerts", Engineering and Technology News, Aug. 2007, 3 pages.

\* cited by examiner

DRUG DELIVERY DEVICE

CROSS REFERENCE TO RELATED APPLICATIONS

The present application is the national stage entry of International Patent Application No. PCT/EP2018/079915, filed on Nov. 1, 2018, and claims priority to Application No. EP 17306518.6, filed on Nov. 3, 2017, the disclosures of which are incorporated herein by reference.

TECHNICAL FIELD

The present disclosure relates to a drug delivery device comprising an audible and/or tactile indicator mechanism.

BACKGROUND

Administering an injection is a process which presents a number of risks and challenges for users and healthcare professionals, both mental and physical. Drug delivery devices typically fall into two categories—manual drug delivery devices or autoinjectors. In a conventional manual device, manual force is required to drive a medicament through a needle. This is typically done by some form of plunger that has to be continuously pressed during the injection. There are numerous disadvantages associated with this approach. For example, if the plunger is released prematurely, the injection will stop and may not deliver an intended dose. Further, the force required to push the plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

It is desirable to administer the full dose in order to achieve full effectiveness of the medicament within the patient.

SUMMARY

The present disclosure relates to an improved drug delivery device.

According to the present disclosure, a drug delivery device comprises at least a housing adapted to receive a cartridge or primary container with a piston and a plunger slidably disposed in the housing and adapted to drive the piston for delivering a drug or a medicament. The device further comprises a drive spring pre-loaded between the housing and the plunger so as to urge the plunger towards a distal direction. Furthermore, an audible and/or tactile indicator, e.g. a resilient force member, is provided, e.g. disposed at a proximal end of the device, in particular at a proximal end of the housing. A trigger mechanism for activating the indicator is provided and arranged between the indicator and the plunger, wherein the trigger mechanism is configured to support the indicator in an initial state of the device and/or during delivery of the medicament and to couple with the plunger to activate the audible and/or tactile indicator at or near an end of delivery, in particular when the plunger is in a distal position.

In particular, the trigger mechanism engages with the plunger to activate the audible and/or tactile indicator at or near the end of delivery of the medicament. In an exemplary embodiment, upon activating of the indicator said indicator disengages from the support of the trigger mechanism.

According to another aspect, as the trigger mechanism is being engaging with the plunger the trigger mechanism is being disengaged from the indicator to activate the indicator. In particular, the indicator can deform or relax when its support is disengaged. For instance, the indicator can disengage from the support by the trigger mechanism.

According to the disclosure, the indicator is engaged, e.g. in contact, with the trigger mechanism in the initial state and during injection. In particular, the trigger mechanism supports the indicator in an initial state, e.g. unbiased state, or in a biased state. Alternatively, the trigger mechanism may hold or press the indicator in or into an initial state, e.g. unbiased state, or in or into a biased state. Furthermore, the trigger mechanism only supports the indicator before its activation.

In particular, the housing may comprise an inner surface forming a cavity configured to retain the cartridge or a drug container or primary container. The primary container comprises an inner surface forming a cavity configured to slidably receive the piston. Due to coupling of the plunger and the piston, the piston moves in the distal direction when the plunger moves in the distal direction for delivering the medicament.

Such a drug delivery device ensures that the trigger mechanism fires or activates the indicator regardless of the length of the plunger. Hence, the length of the plunger could be changed without affecting activation or firing of the indicator. Furthermore, the number of parts, which would have to be replaced to accommodate a change in dose delivered by the drug delivery device, is minimised.

In an exemplary embodiment, the trigger mechanism comprises at least one structure resiliently abutting the plunger. In particular, the at least one structure resiliently abuts the plunger before activating of the indicator. The at least one structure may protrude from an indicator holder towards the plunger. Alternatively, the at least one structure may protrude from the housing towards the plunger. The housing can also be configured to hold the indicator. In this embodiment, the holder may be formed as a part of an inner housing so a separate indicator holder is not required. In detail, the structure may protrude from the housing, for example from an inner part of the housing towards the plunger.

According to another aspect of the present disclosure, the structure may have an inclined surface. The inclined surface ensures guiding and coupling with the plunger. In particular, the structure may comprise a proximal inclined end and a distal stepped edge. The distal stepped edge secures coupling with the plunger.

In an exemplary embodiment, the structure comprises at least one fin.

Furthermore, the plunger may comprise at least one cut-out adapted to receive the at least one structure at or near the end of delivery, in particular when the plunger is in a distal position.

In an exemplary embodiment, the cut-out comprises a lateral inclined edge. The lateral inclined edge supports and ensures catching of the fin. Furthermore, the cut-out may comprise a distal stepped edge. This edge secures the coupling with the fin, in particular with the distal stepped edge of the fin.

In a further exemplary embodiment, the indicator comprises two adjacent fins and the plunger comprises two corresponding adjacent cut-outs adapted to receive the fins.

According to another aspect of the disclosure, a needle sleeve is telescopically coupled to the housing and has an inner surface with at least one radially inwardly protruding guide rail extending in parallel to a longitudinal axis.

Furthermore, the plunger may comprise at least one radially outwardly protruding guide pin. In an exemplary embodiment, the guide pin and the guide rail are configured to engage each other, e.g. coaxially to the longitudinal axis.

According to a further aspect of the disclosure, the guide pin may comprise a guide pin surface engaging a corresponding guide rail surface of the guide rail. In particular, the guide pin surface and the guide rail surface may be oppositely inclined to each other. For example, the guide pin surface and the guide rail surface may be engaged to each other in an angle between 30° and 60°, in particular between 40° and 50°.

In an exemplary embodiment, the guide pin is formed as a protruding boss. The guide pin may comprise an inclined distal end. The inclined distal end ensures correct positioning and alignment, in particular for controlling rotation of the plunger to ensure that the fin will fall into the cut-out.

Furthermore, the guide rail may be formed as a protruding elongated rib extending in parallel to the longitudinal axis. The elongated rib ensures a guiding of the pin during delivery of the medicament.

Moreover, the drug delivery device may be an auto-injector, a pen-injector or a syringe. The primary container may be prefilled with a drug.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector.

The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
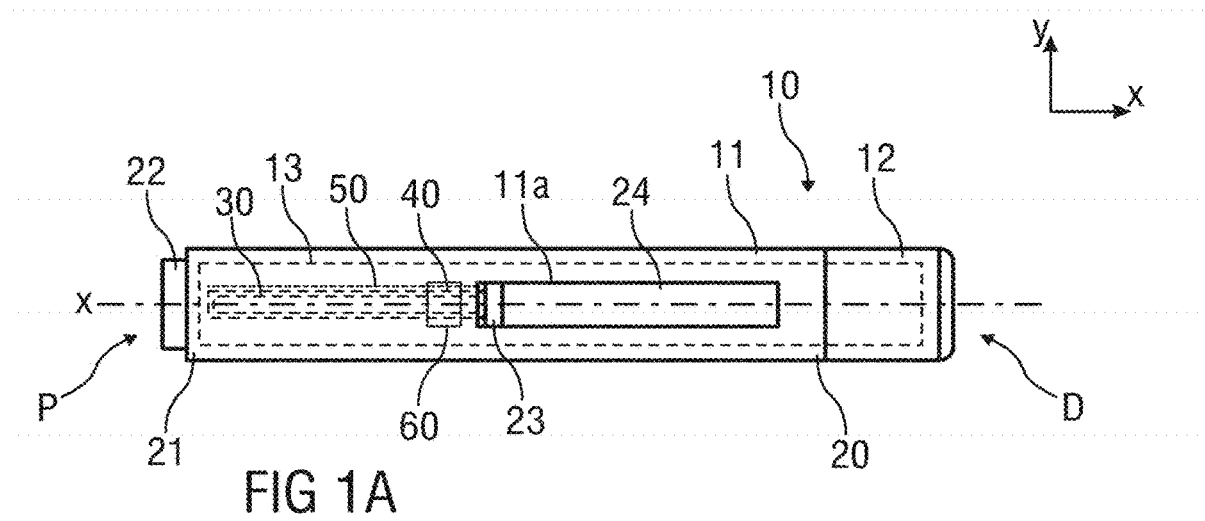
FIGS. 1A, 1B are schematic views of a drug delivery device comprising a tactile and/or audible indicator.
Figure 1B:
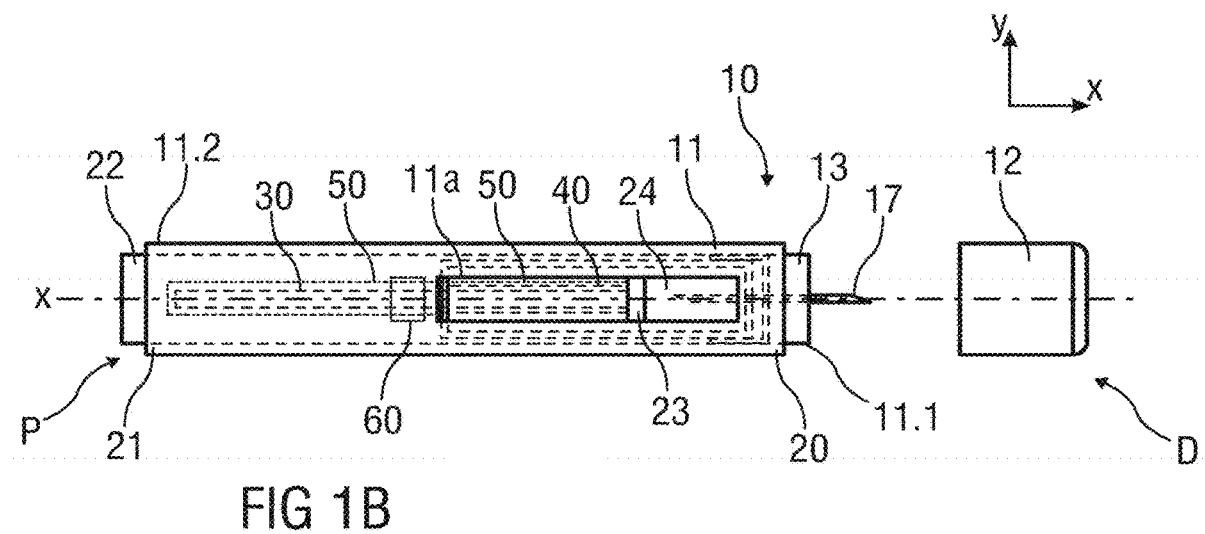

According to some embodiments of the present disclosure, an exemplary drug delivery device 10 is shown in FIGS. 1A and 1B.

Device 10, as described above, is configured to inject a drug or medicament into a patient's body.

Device 10 includes a housing 11 which typically contains a reservoir or cartridge containing the medicament to be injected (e.g., a syringe 24 or a container) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from distal region 20 of housing 11.

Insertion of the needle 17 can occur via several mechanisms. For example, the needle 17 may be fixedly located relative to housing 11 and initially be located within an extended needle sleeve 13.

Proximal movement of the sleeve 13 by placing a distal end of sleeve 13 against a patient's body and moving housing 11 in a distal direction or sleeve 13 in a proximal direction will uncover the distal end of needle 17. Such relative movement allows the distal end of needle 17 to extend into the patient's body. Such insertion is termed "manual" insertion as the needle 17 is manually inserted via the patient's manual movement of the sleeve 13 relative to the housing 11 and the needle 17 or reverse.

Another form of insertion is "automated," whereby the needle 17 moves relative to housing 11. Such insertion can be triggered by movement of sleeve 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a sleeve trigger mechanism, e.g. provided by pushing the needle sleeve 13 inside the housing when the drug delivery device is put onto an injection side.

Other manual or automated features can include drug injection, automatic needle insertion or needle retraction, or both. Injection is the process by which a bung or piston 23 is moved from a proximal location within a cartridge, container or syringe 24 to a more distal location within the syringe 24 in order to force a medicament from the syringe 24 through needle 17.

In some embodiments, an energy source, e.g. a drive spring 30 is arranged in a plunger 40 and is under compression before device 10 is activated. A proximal end of the drive spring 30 can be fixed within proximal region 21 of housing 11, and a distal end of the drive spring 30 can be configured to apply a compressive force to a proximal surface of piston 23. Following activation, at least part of the energy stored in the drive spring 30 can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe 24 within the housing 11 is moved in a proximal direction relative to the housing 11. This proximal movement can be achieved by using a retraction spring (not shown), located in the distal region 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11a through which the syringe 24 can be monitored.

In the present specification, the term "distal section/end" refers to the section/end of the device 10, or the sections/ends of the components thereof, which during use of the device 10 is located closest to a medicament delivery site of a patient. Correspondingly, the term "proximal section/end" refers to the section/end of the device 10, or the sections/ends of the components thereof, which during use of the device 10 is pointing away from the medicament delivery site of the patient.

In the shown exemplary embodiments, the drug delivery device 10 comprises the housing 11 with a front case 11.1 and a rear case 11.2. The front case 11.1 is adapted to hold the medicament container or primary container 24, such as a syringe. The medicament primary container is referred to hereinafter as the "syringe 24". The syringe 24 may be a pre-filled syringe, in particular a 1.0 ml pre-filled syringe, containing a medicament and having the needle 17 arranged at a distal end of the syringe 24. In another exemplary embodiment, the medicament container may be a primary container which includes the medicament and engages a removable needle (e.g., by threads, snaps, friction, etc.).

The drug delivery device 10 may be configured as an autoinjector or as a manual drug delivery device.

Moreover, the drug delivery device 10 comprises an audible and/or tactile indicator 50 providing an audible and/or tactile indication to a user of the device 10 at the end of delivery of the medicament. In particular, the indicator 50 produces an audible and/or tactile feedback for a user or patient indicating completion of medicament delivery. In other words: The indicator 50 is provided to indicate to a user or a patient that the full dose of medicament was spent.

In an exemplary embodiment, the indicator 50 is disposed at the proximal end P of the device 10. For example, the indicator 50 is arranged at a proximal end of the housing 11 and inside the housing 11.

Further, a trigger mechanism 60 is arranged between the indicator 50 and the plunger 40. The trigger mechanism 60 is configured to support the indicator 50 in an initial state of the device 10, for example during storage and transportation as well as during delivery of the medicament and to couple with the plunger 40 to activate the indicator 50 at an end of delivery.

In particular, the trigger mechanism 60 engages with the plunger 40 to activate the audible and/or tactile indicator 50 at or near the end of delivery of the medicament.

In an exemplary embodiment, upon activating of the indicator 50, said indicator 50 can disengage from the support of the trigger mechanism 60. In particular, as the trigger mechanism 60 is being engaging with the plunger 40 near or at the end of delivery of the medicament, the trigger mechanism 60 is being disengaged from the indicator 50 to activate it. For example, the indicator 50 can deform or relax when its support is disengaged. For instance, the indicator 50 can disengage from the support by the trigger mechanism 60.

For example, the indicator 50 is engaged, e.g. in contact, with the trigger mechanism in the initial state and during injection. In particular, the trigger mechanism 60 supports the indicator 50 in an initial state, e.g. unbiased state, or in a biased state. Alternatively, the trigger mechanism 60 may hold or press the indicator 50 in or into an initial state, e.g. unbiased state, or in or into a biased state. Furthermore, the trigger mechanism 60 only supports the indicator 50 before its activation and releases it upon activating.

In an exemplary embodiment, the indicator 50 is formed as a biasing member, a spring, a laminated spring, a flat spring, a plate spring or a leaf spring.

In an exemplary embodiment, the trigger mechanism 60 comprises at least one structure, e.g. a protrusion, a flap, projection, resiliently abutting the plunger 40. In particular, the at least one structure resiliently abuts the plunger 40 before activating of the indicator 50.

In particular, a part of the trigger mechanism 60, e.g. one surface side, for instance an outer side of the trigger mechanism 60, abuts and supports the indicator 50 and an opposite surface side, e.g. an inner side of the trigger mechanism 60, abuts the plunger 40 before activating of the indicator 50, e.g. before and during delivery of the medicament. Upon activating of the indicator 50, the trigger mechanism 60 disengages from indicator 50 and a part of the trigger mechanism 60 couples or engages with the plunger 40.

FIGS. 2A to 4C respectively show embodiments of the indicator 50 which will be described further below.

Figure 2A:
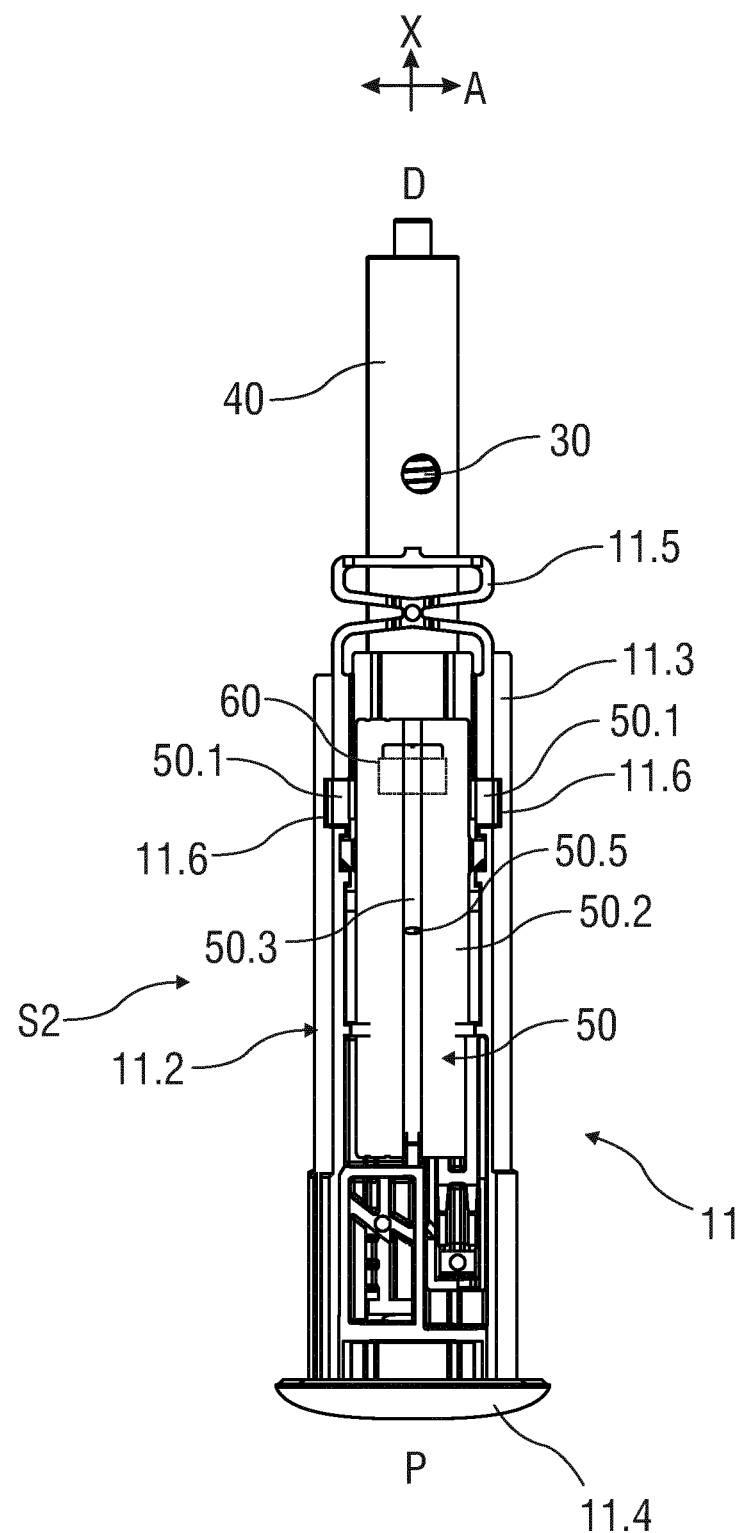
FIG. 2A is a schematic perspective view and a longitudinal section of a proximal end of the drug delivery device.

FIG. 2A shows a longitudinal section of an exemplary embodiment of the rear case 11.2. In an assembled state, the rear case 11.2 serves for example as a drive subassembly 11.4 of the drug delivery device 10.

The drive sub assembly 11.4 is a sub assembly of the drug delivery device 10 and comprises the components required to deliver the medicament. The drive subassembly 11.4 comprises for example the rear case 11.2, the plunger 40, the drive spring 30 and the indicator 50. The drug delivery device 10 further comprises a front sub assembly (not shown separately) to allow for flexibility as to the time and location of manufacture of the subassemblies and final assembly with the syringe 24.

According to the present embodiment, the rear case 11.2 comprises two support arms 11.3 adapted to support an axial position of the syringe 24 during storage, transportation and medicament delivery. The support arms 11.3 project distally from a proximal case end 11.4 of the rear case 11.2. The rear case 11.2 further comprises additional flexible projections 11.5 that project distally from the distal end of the rear case 11.2 as well. In detail, the flexible projections 11.5 project distally from the distal end of the support arms 11.3.

The projections 11.5 are adapted to damp impact forces and thus to stabilize the syringe 24 during storage, transportation and delivery.

In an exemplary embodiment, the indicator 50 is arranged on the housing 11, in particular on the rear case 11.2. In detail, the indicator 50 is arranged on an outer side of at least one of the support arms 11.3. In this embodiment, in which the indicator 50 is arranged on the rear case 11.2, the trigger mechanism 60 is also arranged on the rear case 11.2. In detail, the trigger mechanism 60 is arranged on an inner side of the support arm 11.3 and thus on a side opposite the side of the support arms 11.3 where the indicator 50 is arranged. The trigger mechanism 60 is adapted to damp impact forces and thus to stabilize the indicator 50 in its biased state during storage, transportation, and medicament delivery.

In an alternative embodiment, the indicator 50 may arranged on a holder (not shown) which is arranged in the housing 11. The trigger mechanism 60 may then also be arranged on the holder in a similar manner as on the rear case 11.2.

In an assembled state, the indicator 50 is arranged within the device 10 at the proximal end P of housing 11. A proximal end of the plunger 40 is at least partially received within the rear case 11.2. The rear case 11.2 is closed at its outer proximal end 11.4.

In detail, the indicator 50 is held in the rear case 11.2 such that the longitudinal axis X is in parallel with a longitudinal extension of the drug delivery device 10. The indicator 50 may be coupled to the drug delivery device 10 by a snap connection, wherein one or more of the tabs 50.1 are engaged within a number of corresponding openings 11.6 in the rear case 11.2. In another exemplary embodiment, the indicator 50 is held in the rear case 11.2 by a frictional connection, such as a screw or rivet connection or interference fit.

Figure 2B:
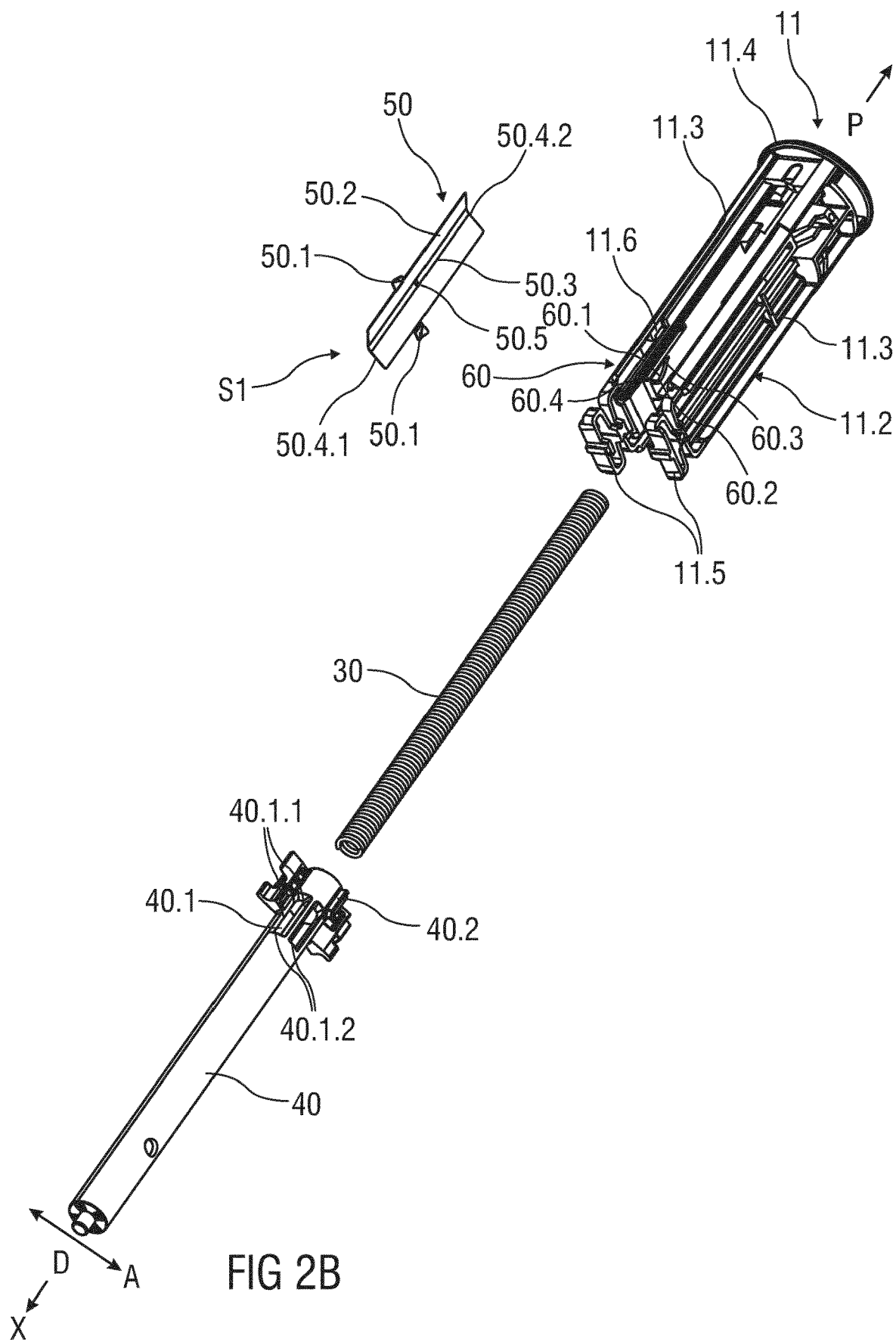
FIG. 2B is a schematic exploded view of a proximal end of the drug delivery device with a trigger mechanism arranged between an indicator and a plunger.
Figure 2C:
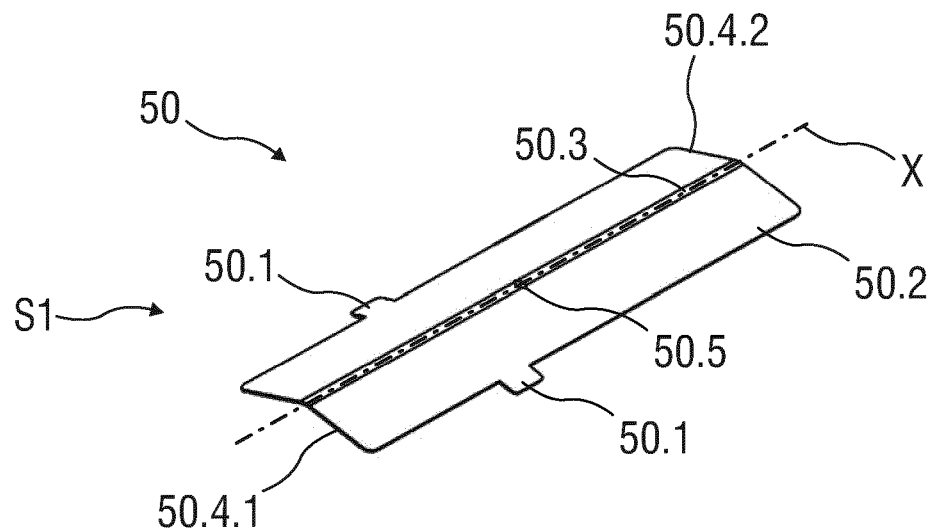
FIGS. 2C, 2D are schematic perspective view of an indicator in an initial state and in a primed state.
Figure 2D:
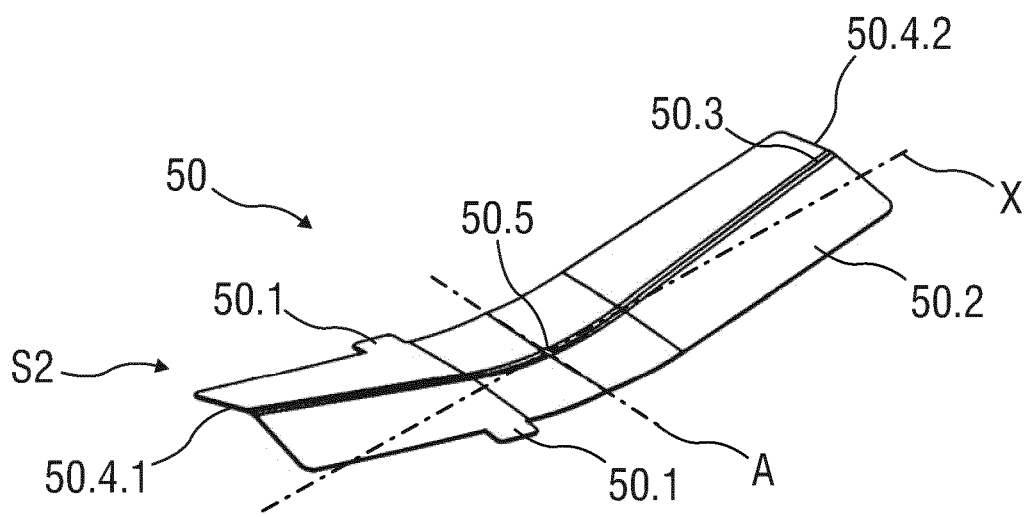

FIGS. 2A and 2C show the indicator 50 in a pre-assembly state and initial or relaxed state S1. FIG. 2B shows the indicator 50 in an assembly state in the rear case 11.2 and in a primed or biased state S2 and FIG. 2D shows the indicator in the biased state S2, too.

The indicator 50 comprises a resilient force member 50.2, e.g. having a substantially rectangular shape, comprising a longitudinal axis running in parallel to the longest side of the outer circumference of the resilient force member 50.2. In other embodiments, the resilient force member 50.2 may have a triangular shape or any other geometrical shape suitable to couple the indicator 50 to the device 10, e.g. an autoinjector.

The resilient force member 50.2 may be designed as a monostable leaf spring comprising a resilient material, e.g. spring steel or spring plastic. Thus, the resilient force member 50.2 is capable of residing in two states. That is, the resilient force member 50.2 may assume two different conformations, one of them stable with limited or no application of an external force and the other one unstable. For example, these two states can include a first or relaxed state S1 (or pre-assembly state, or trigged state, or initial state), in which the resilient force member 50.2 has a first conformation. In a second or biased state S2 (or primed state), the resilient force member 50.2 can have a second conformation. In FIG. 2A, the resilient force member 50.2 is in the relaxed state S1 which can correspond to the pre-assembly state as well as to a state at the end of medicament delivery.

In a possible embodiment, the resilient force member 50.2 comprises a longitudinal bend 50.3. The longitudinal bend 50.3 can be arranged generally in the centre of the resilient force member 50.2 running in parallel to the longitudinal axis X. The longitudinal bend 50.3 can divide the indicator 50 into two wing-shaped sections angled to each other with an angle less than 180 degrees. In in the illustrated perspective of FIGS. 2A and 2C, the wing-shaped sections are angled downwards.

Furthermore, the resilient force member 50.2 can comprise one or more tabs 50.1 projecting perpendicularly to the longitudinal axis X from the outer circumference. Specifically, the resilient force member 50.2 can include one, two, three, four or more tabs 50.1.

As shown in FIGS. 2A to 2D, the resilient force member 50.2 includes two tabs 50.1, wherein one of the tabs 50.1 is arranged opposite the other tab 50.1. In another embodiment (not shown), the resilient force member 50.2 can include pairs of tabs 50.1 located generally opposite each other. The pairs of tabs 50.1 are arranged spaced to each other in the direction of the longitudinal axis X. In another exemplary embodiment, the number and arrangement of the tabs 50.1 may differ from the shown exemplary embodiment. In an exemplary embodiment, the tabs 50.1 may be angled with respect to the wing-shaped sections to facilitate assembly of the drug delivery device 10.

For assembling the indicator 50 into the drug delivery device 10, the resilient force member 50.2 is bent in the centre about an axis A running perpendicular to the longitudinal axis X. The bending angle may be less than 90 degrees. This bending is achieved by applying a predetermined force onto or near the centre point of the resilient force member 50.2 when engaging the tabs 50.1 within the openings 11.6 in the rear case 11.2. As a result, the resilient force member 50.2 changes from the relaxed state S1 into the biased state S2. Two ends 50.4.1, 50.4.2 of the resilient force member 50.2 at opposite ends along the longitudinal axis X are angled upwards from the centre point 50.5 in the illustrated perspective of FIG. 2C, which shows the biased state S2. Hence, the biased state S2 corresponds with the primed state, wherein the resilient force member 50.2 stores a certain amount of energy.

After removing the applied force, the resilient force member 50.2 is held in the biased state S2 as it is shown in FIG. 2C and described below.

The resilient force member 50.2 is in the biased state S2 and held in the rear case 11.2 by the snap connection as described above. The distally pointing end 50.4.1 of the resilient force member 50.2 and the biased state S2 of the indicator 50 is supported and activated by the trigger mechanism 60 arranged on the support arm 11.3 as described further below.

The proximally pointing end 50.4.2 of the resilient force member 50.2 is free and not in contact with any other component and located above the trigger mechanism 60 or another section of the rear case 11.2.

After changing from the relaxed state S1 into the biased state S2 as described before, only a small force may be required to hold the resilient force member 50.2 in the biased state S2. This is achieved by the longitudinal bend 50.3 that provides a bent cross section of the resilient force member 50.2 which buckles into a new configuration by changing from the relaxed state S1 into the biased state S2. In this configuration, a stiffness of the material structure is significantly reduced and thus only a small holding force is required to maintain the resilient force member 50.2 in the biased state S2.

In detail, the trigger mechanism 60 comprises at least one structure 60.1 resiliently abutting the plunger 40. The structure 60.1 may protrude from an indicator holder towards the plunger 40. The structure 60.1 may be formed as a fin. The protruding structure 60.1 is referred to hereinafter as "fin 60.1". Due to the support of the fin 60.1 on the plunger 40 during storage, transportation and delivery, the indicator 50 is supported in its biased state S2, too.

In detail, the at least one fin 60.1 protrudes from the housing 11, in particular from the rear case 11.2, e.g. from its inner support arm 11.3 towards the plunger 40. The support arm 11.3 is formed as an indicator holder. The indicator 50 and the fin 60.1 are arranged on opposite surface side of the support arm 11.3. The indicator 50 is held on a surface side of arm 11.3 facing to the outer housing 11. The fin 60.1 is formed on the opposite side of the arm 11.3 facing inwards and towards to the plunger 40.

Alternatively, the fin 60.1 may protrude from a separate indicator holder (not shown) towards the plunger 40. The separate indicator holder may be arranged between the indicator 50 and the plunger 40 within the housing 11.

In an exemplary embodiment, the fin 60.1 has an inclined surface 60.2. In particular, an upper or top surface of the fin 60.1 is rounded or inclined. The inclined surface 60.2 ensures guiding along the plunger 40 during delivery of the medicament.

Further, the fin 60.1 may comprise a proximal inclined end 60.3 and a distal stepped edge 60.4. The proximal inclined end 60.3 allows an easy coupling of the fin 60.1 with the plunger 40. The distal stepped edge 60.4 is configured to secure the coupling of the fin 60.1 with the plunger 40.

According to another aspect of the disclosure, the plunger 40 comprises at least one cut-out 40.1 adapted to receive the at least one fin 60.1 at the end of delivery, for example when the plunger 40 is in the distal position. Due to the fin 60.1 falling into the cut-out 40.1 at the end of delivery, the indicator 50 relaxes and generates an acoustic noise. Additionally, the indicator 50 may be configured to generate a tactile feedback on the outer housing 11, too. The indicator 50 thus provides an end-of-delivery feedback to a user.

Furthermore, the cut-out 40.1 may comprise a lateral inclined edge 40.1.1. Such a lateral inclined edge 40.1.1 facilitates the fin 60.1 falling into the cut-out 40.1. The cut-out 40.1 may further comprise a distal stepped edge 40.1.2. The distal stepped edge 40.1.2 corresponds with the distal stepped edge 60.4 of the fin 60.1 to facilitate the coupling of the fin 60.1 and the cut-out 40.1.

In the exemplary embodiment, the trigger mechanism 60 comprises two adjacent fins 60.1 and the plunger 40 comprises two correspondingly adjacent cut-outs 40.1 adapted to receive the fins 60.1. The two fins 60.1 are arranged spaced to each other in the direction of the transversal direction. The pair of fins 60.1 protrudes from the inner surface of the rear case 11.2 facing the plunger 40 when received inside the housing 11. The radially inwardly protruding and adjacent fins 60.1 abut the plunger 40, thereby supporting the resilient force member 50.2 in its biased state S2. In another exemplary embodiment, the number and arrangement of the fins 60.1 may differ from the shown exemplary embodiment.

In another exemplary embodiment, the number and arrangement of the indicators 50 and trigger mechanism 60 may differ from the shown exemplary embodiment. The device 10 may comprise two trigger mechanism 60 and two indicators 50 described above. Each of a pair of trigger mechanism 60 and indicators 50 may be arranged on one of the support arms 11.3 of the rear case 11.2.

For delivering a medicament, as can be seen in more detail in an exploded view in FIG. 2B, the plunger 40 is driven by a drive spring 30 that is arranged between the plunger 40 and the rear case 11.2. The drive spring 30 may be arranged within the plunger 40 and be pre-loaded such as to urge the plunger 40 towards the distal end D of the device 10.

Figure 3A:
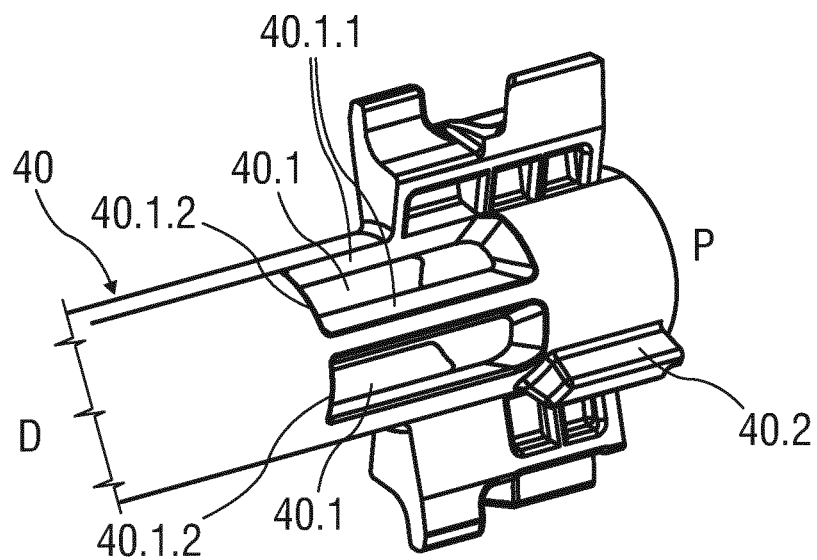
FIG. 3A is a schematic perspective view of a proximal end of a plunger with cut-outs.
Figure 3B:
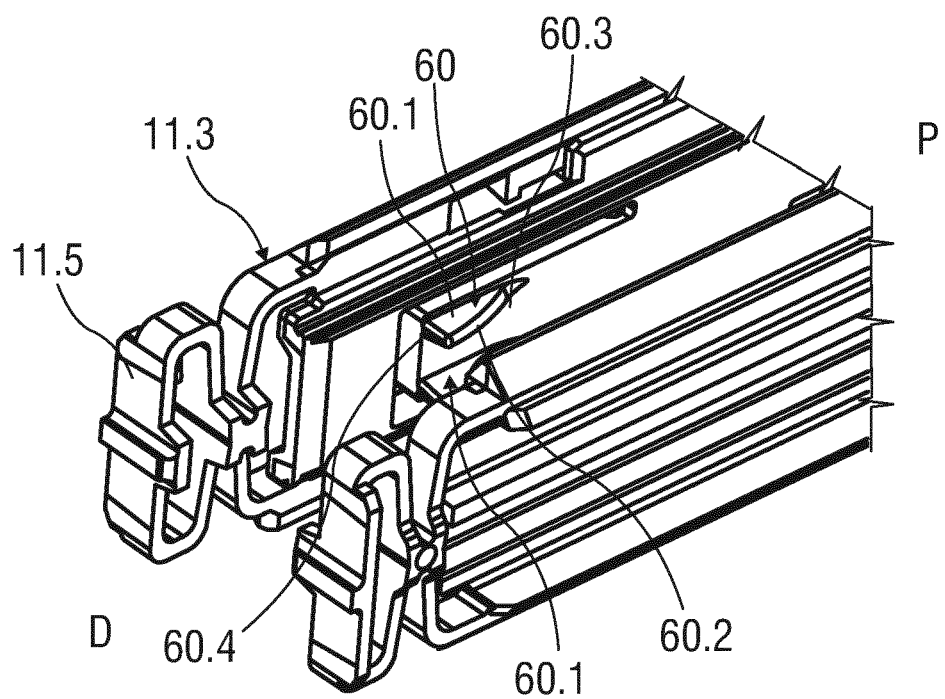
FIG. 3B is a schematic perspective view of a distal end of a rear case.

As can be seen in detail in FIGS. 3A and 3B, two circumferentially adjacent cut-outs 40.1 corresponding to the adjacent fins 60.1 of the trigger mechanism 60 are arranged near the proximal end P of the plunger 40. The plunger 40 is aligned in an angular position relative to the rear case 11.2 such that each of the fins 60.1 is axially aligned with its corresponding cut-out 40.1. During the injection, the plunger 40 is translated in a distal direction towards a distal position until reaching a position at the end of the injection, where the fins 60.1 will snap into the cut-outs 40.1. Thereby, the resilient force member 50.2 will relax from its biased state S2 into its relaxed state S1. An audible and/or tactile click emitted upon this relaxation indicates the end of the injection process to the user.

As shown in FIG. 3B, the fins 60.1 are formed in the shape of shark fins with a proximally arranged inclined end 60.3 and with a distally arranged stepped edge 60.4. Thereby, the resilient force member 50.2 relaxes immediately with a sharp click noise, when the plunger 40 reaches its distal end position.

Figure 4A:
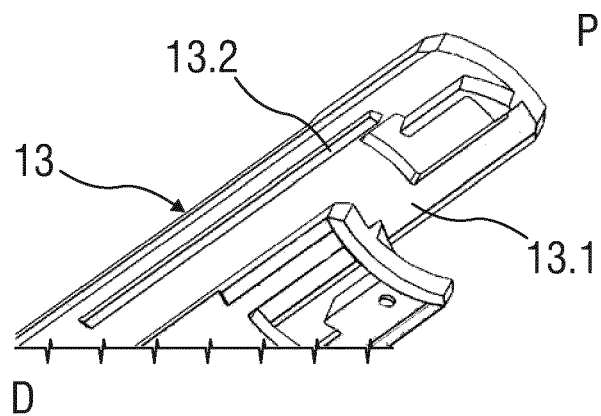
FIG. 4A is a schematic perspective view of a proximal end of a sleeve with a guide rail.
Figure 4B:
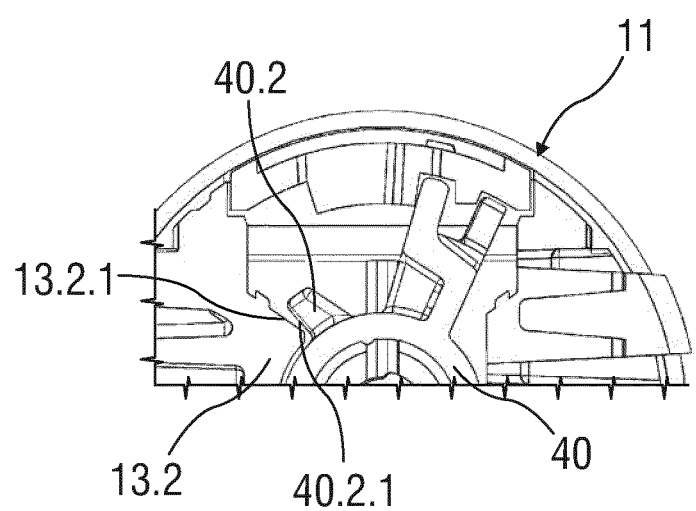
FIG. 4B is a schematic cross section of a proximal end of a drug delivery device with a plunger comprising a protruding guide pin.
Figure 4C:
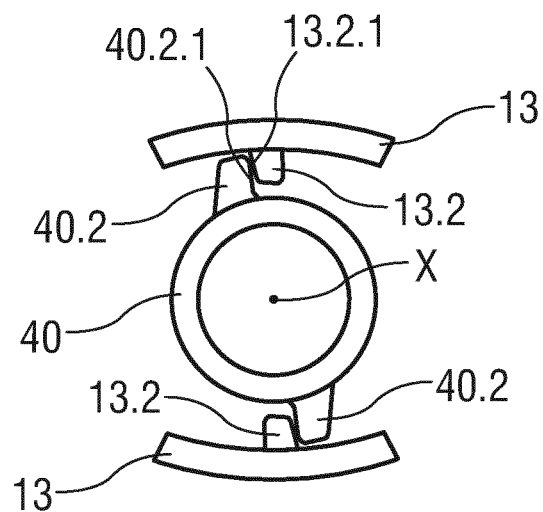
FIG. 4C is a schematic view of a guiding mechanism for guiding a plunger along a needle sleeve.

FIG. 4A shows a further aspect of the disclosure concerning the sleeve 13 comprising a guide rail 13.2. FIG. 4B shows a guide pin 40.2 corresponding to the guide rail 13.2 and protruding from a proximal end of the plunger 40. FIG. 4C is a schematic view of a guiding mechanism for guiding the plunger 40 along the needle sleeve 13 due to the interrelation of guide pin 40.2 and guide rail 13.2.

In detail, the needle sleeve 13 is telescopically coupled to the housing 11 and has an inner surface 13.1 with at least one radially inwardly protruding guide rail 13.2 extending in parallel to the longitudinal axis X. The guide rail 13.2 is formed for example as a protruding rib elongated parallel to the longitudinal axis X.

Furthermore, the plunger 40 may comprise at least one radially outwardly protruding guide pin 40.2. In an exemplary embodiment, the guide pin 40.2 and the guide rail 13.2 are configured to engage each other, e.g. coaxially to the longitudinal axis X. In particular, the guide pin 40.2 engages the at least one guide rail 13.2 as best seen in FIG. 4C.

In more detail, the guide pin 40.2 may comprise a guide pin surface 40.2.1 engaging a corresponding guide rail surface 13.2.1 of the guide rail 13.2.

Furthermore, the guide pin surface 40.2.1 and the guide rail surface 13.2.1 may be oppositely inclined to each other. For example, the guide pin surface 40.2.1 and the guide rail surface 13.2.1 are engaged to each other in an angle between 30° and 60°, in particular between 40° and 50°.

Figure 4D:
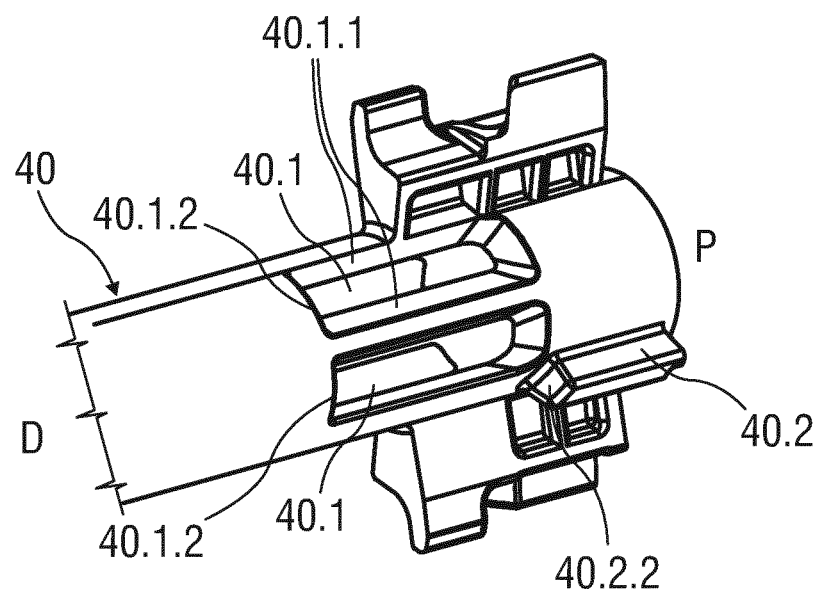
FIG. 4D is a schematic view of a proximal end of a plunger with a guide pin.

In an exemplary embodiment, the guide pin 40.2 is formed as a protruding boss as shown in FIG. 4D. The guide pin 40.2 may comprise an inclined distal end 40.2.2. The inclined distal end 40.2.2 ensures correct positioning and alignment, in particular controlling rotation of the plunger 40 to ensure that the fin 60.1 will fall into the cut-out 40.1.

Moreover, the drug delivery device 10 may be an autoinjector, a pen-injector or a syringe. The primary container or syringe 24 may be prefilled with a drug.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 10 drug delivery device
11 housing
11.1 front case
11.2 rear case
11.3 support arm
11.4 proximal end
11.5 projection
11.6 opening
12 cap assembly
13 needle sleeve
13.1 inner surface
13.2 guide rail
13.2.1 surface
17 needle
20 distal region of the drug delivery device
21 proximal region of the drug delivery device
22 button
23 piston
24 primary container
30 energy source, e.g. drive spring
40 plunger
40.1 cut-out
40.1.1 lateral inclined surface
40.1.2 distal stepped edge
40.2 guide pin
40.2.1 surface
40.2.2 inclined end
50 indicator
50.1 tab
50.2 resilient force member
50.3 bend
50.4.1, 50.4.2 end
60 trigger mechanism
60.1 structure (e.g. fin)
60.2 inclined surface
60.3 proximal inclined end
60.4 distal stepped edge
D distal end
P proximal end

The invention claimed is:

1. A drug delivery device comprising:
a housing adapted to receive a container with a piston;
a plunger slidably disposed in the housing and adapted to drive the piston for delivering a medicament;
a drive spring pre-loaded between a proximal portion of the housing and the plunger so as to urge the plunger in a distal direction;
an audible and/or tactile indicator configured to provide an indication to a user at or near an end of delivery of the medicament; and
a trigger mechanism arranged between the audible and/or tactile indicator and the plunger,
wherein the trigger mechanism is configured to
support the audible and/or tactile indicator in an initial state of the drug delivery device and during delivery of the medicament, and
couple with the plunger to activate the audible and/or tactile indicator at or near the end of delivery of the medicament.

2. The drug delivery device according to claim 1, wherein upon activation of the audible and/or tactile indicator, the audible and/or tactile indicator disengages from support by the trigger mechanism.

3. The drug delivery device according to claim 1, wherein the trigger mechanism comprises at least one structure resiliently abutting the plunger.

4. The drug delivery device according to claim 3, wherein the at least one structure protrudes from an indicator holder towards the plunger.

5. The drug delivery device according to claim 3, wherein the at least one structure protrudes from the housing towards the plunger.

6. The drug delivery device according to claim 3, wherein the at least one structure has an inclined surface.

7. The drug delivery device according to claim 3, wherein the at least one structure comprises a proximal inclined end, a distal stepped edge, and/or at least one fin or rib.

8. The drug delivery device according to claim 3, wherein the plunger provides at least one cut-out adapted to receive the at least one structure at or near the end of delivery of the medicament.

9. The drug delivery device according to claim 8, wherein the at least one cut-out comprises a lateral inclined edge and/or a distal stepped edge.

10. The drug delivery device according to claim 1, wherein the trigger mechanism comprises two adjacent structures, and wherein the plunger comprises two correspondingly adjacent cut-outs adapted to receive the two adjacent structures.

11. The drug delivery device according to claim 1, wherein a needle sleeve is telescopically coupled to the housing and has an inner surface with at least one radially inwardly protruding guide rail extending in parallel to a longitudinal axis.

12. The drug delivery device according to claim 11, wherein the plunger comprises at least one radially outwardly protruding guide pin configured to engage the at least one radially inwardly protruding guide rail.

13. The drug delivery device according to claim 12, wherein the at least one radially outwardly protruding guide pin is formed as a protruding boss and/or comprises an inclined distal end.

14. The drug delivery device according to claim 11, wherein the at least one radially inwardly protruding guide rail is formed as a protruding elongated rib in parallel to the longitudinal axis.

15. The drug delivery device according to claim 1, comprising the container, wherein the container is prefilled with a drug.

16. The drug delivery device according to claim 1, wherein the drug delivery device is an auto-injector, a pen-injector, or a syringe.

17. An assembly for a drug delivery device, the assembly comprising:
- a plunger adapted to deliver medicament from the drug delivery device;
- an audible and/or tactile indicator configured to provide an indication to a user at or near an end of delivery of the medicament from the drug delivery device; and
- a trigger mechanism configured to be arranged between the audible and/or tactile indicator and the plunger of the drug delivery device, the trigger mechanism comprising a resilient structure abutting the plunger, wherein the trigger mechanism is configured to
- support the audible and/or tactile indicator in an initial state of the assembly and during delivery of the medicament, and
- couple with the plunger to activate the audible and/or tactile indicator at or near the end of delivery of the medicament.

18. The assembly of claim 17, wherein the resilient structure of the trigger mechanism protrudes from an indicator holder towards the plunger.

19. The assembly of claim 17, wherein the resilient structure has an inclined surface configured to be guided along the plunger during delivery of the medicament.

20. The assembly of claim 19, wherein the resilient structure comprises a proximal inclined end, a distal stepped edge, and/or at least one fin or rib.

* * * * *